United States Patent [19]
Horrobin

[11] Patent Number: 5,223,271
[45] Date of Patent: Jun. 29, 1993

[54] LITHIUM TREATMENT

[75] Inventor: David F. Horrobin, Lythe Hill Park, England

[73] Assignee: Efamol Holdings PLC, Surrey, England

[21] Appl. No.: 765,008

[22] Filed: Sep. 24, 1991

[30] Foreign Application Priority Data

Oct. 31, 1990 [GB] United Kingdom ............... 9023701

[51] Int. Cl.$^5$ .................... A61K 31/20; A61K 33/00; A61K 33/14
[52] U.S. Cl. .................... 424/677; 424/715; 514/274; 514/560; 514/574
[58] Field of Search ............ 514/574, 560, 578, 274; 424/677, 715

[56] References Cited

U.S. PATENT DOCUMENTS

| | | | |
|---|---|---|---|
| 3,639,625 | 2/1972 | Sherwin | 424/317 |
| 4,328,243 | 5/1982 | Horrobin et al. | 424/301 |
| 4,386,072 | 5/1983 | Horrobin et al. | 424/127 |
| 4,810,497 | 3/1989 | Horrobin | 424/153 |

FOREIGN PATENT DOCUMENTS

| | | |
|---|---|---|
| 0085579 | 8/1983 | European Pat. Off. |
| 0132126 | 1/1985 | European Pat. Off. |
| 0135312 | 3/1985 | European Pat. Off. |
| 0289204 | 11/1988 | European Pat. Off. |
| 0305097 | 3/1989 | European Pat. Off. |

OTHER PUBLICATIONS

Arnold, Harry L., Jr., Odom, Richard B., and James, William D., Andrews' Diseases of the Skin; Clinical Dermatology Eighth Edition, 1990 Version, pp. 461–463.

Skinner, G. R. B. et al., "Lithium ointment for genital herpes," *The Lancet*, vol. 2, No. 8334, 30 Jul. 1982, p. 288.

Skinner, G. R. B. et al., "The effect of lithium chloride on the replication of Herpes simplex virus," *Medical Microbiology and Immunology*, vol. 168, pp. 139–148.

Fields, B. N. et al., "Molluscum contagiosum", *Fields Virology*, vol. 2, 2nd edition, Raven Press, New York, US, 1990, pp. 2130–2121.

White, D. O. et al., "Poxviruses," *Medical Virology*, 3rd edition, Academic Press, London, GB, 1986, pp. 433–443.

Barkow, R. et al., "Viral infections of the skin," *The Merck Manual of Diagnoses and Therapy*, 15th edition, Merck & Co., Inc., Rahway, N.J., 1987, pp. 2274–2277.

Primary Examiner—Leonard Schenkman
Attorney, Agent, or Firm—Foley & Lardner

[57] ABSTRACT

The present invention provides a method of treatment and/or prophylaxis of the human or animal body to combat Molluscum Contagiosum, said treatment comprising topically administering a therapeutically or prophylactically effective amount of a physiologically acceptable lithium compound to affected areas on said body.

It also extends to pharmaceutical compositions comprising a physiologically acceptable lithium compound together with at least one keratolytic and/or skin penetration assisting agent and at least one pharmaceutically acceptable carrier or excipient.

9 Claims, No Drawings

LITHIUM TREATMENT

The present invention relates to the treatment of skin disorders and in particular to a new medical use for lithium in the treatment of Molluscum Contagiosum.

Molluscum Contagiosum is a common infectious skin disease caused by a pox virus. It occurs predominantly in children and is characterised by the appearance on the body of lobulated epidermal outgrowths or lesions. These lesions, which are the result of excessive cellular proliferation stimulated in the keratinocyte layer by virus which has entered through the skin, appear as white shining papules, 5-10 mm in diameter.

Each lesion, which may have a central pore, contains within its center dead skin cells which have been killed by the virus.

Infections commonly last for 6-12 months but the condition can in certain cases persist for as long as 3-4 years. During this time, new crops of lesions appear, each lesion growing slowly for 6-12 weeks and persisting for an average of 3-4 months.

At present there is no drug treatment for Molluscum Contagiosum; the virus is resistant to the commonly used anti-viral agents which are effective in treating other viral infections and the disease is treated only by surgical removal of the lesions, e.g., by cryotherapy. This can be painful and distressing, particularly for children, and does not of course prevent the reappearance of fresh lesions.

A need therefore exists for an improved method of treating Molluscum Contagiosum and particularly for a treatment which acts at the level of the underlying condition, i.e. by combatting the infecting virus.

We have now surprisingly found that lithium is particularly useful in the treatment of Molluscum Contagiosum. In particular, our studies have shown that lesions on infected individuals are reduced in number and eventually disappear upon topical application of lithium-containing preparations to the affected area, and that the treated area remains clear. In other words, the reappearance of new lesions is prevented.

In one aspect the present invention therefore provides the use of a physiologically acceptable lithium compound, e.g., a water and/or lipid soluble lithium salt, in the manufacture of a medicament for use in the treatment and/or prophylaxis of Molluscum Contagiosum.

In a second aspect there is provided a method of treatment and/or prophylaxis of the human or animal body to combat Molluscum Contagiosum, said treatment comprising topically administering a physiologically acceptable lithium compound to affected areas on said body.

A third aspect of the invention provides use of a physiologically acceptable lithium compound for the treatment and/or prophylaxis of Molluscum Contagiosum.

In the medical field, lithium is known primarily for its therapeutic efficacy in a variety of mental and psychiatric disorders, most notably manic-depressive illness, but including also schizophrenia, alcoholism and certain dementias.

More recently lithium has been proposed for the treatment of Herpes infections and certain dermatitis skin conditions, as described for example in EP-A 0135312 and EP-A 0132126.

It is widely acknowledged, however, that lithium has toxic side effects and that the margin between therapeutic efficacy and toxicity is narrow. Indeed, it is usual to administer lithium only under close medical supervision.

Thus, in the absence of a strong positive indication of a beneficial activity against a given condition, lithium is not a drug which would be routinely administered as a matter of choice.

It was not therefore an obvious candidate in the search for a therapy for Molluscum Contagiosum. Moreover, its efficacy in this regard was both unpredictable and surprising; a positive effect on one viral infection cannot readily be extrapolated to a prediction of a similar effect on another. Thus, the efficacy of lithium in treating Herpes infections provided no expectation of a similar efficacy in treating Molluscum Contagiosum. This is borne out by observations that acyclovir, the most clinically effective drug in treating Herpes, has no effect on Molluscum Contagiosum.

Lithium may be administered according to the invention in any form which will effectively deliver it to the virally infected area, although inorganic and organic salts are generally preferred. Suitable examples of organic and inorganic salts includes lithium succinate, lithium chloride, lithium carbonate and lithium orotate, lithium succinate being generally preferred.

It may also be useful in certain circumstances to administer the lithium in the form of a salt with a polyunsaturated fatty acid, preferably a $C_{18-22}$ polyunsaturated fatty acid such as gammalinolenic or dihomogammalinolenic acid. This has the benefit that, being in a form which is both water and lipid soluble, the lithium is more effectively delivered across cell membranes, and at the same time can be easily formulated into aqueous-based non-greasy compositions.

Lithium is generally employed according to the present invention in the form of any pharmaceutical formulation suitable for topical administration. Thus for example, topical pharmaceutical compositions for use according to the present invention may be formulated in conventional manner as ointments, creams, lotions, gels, sprays, salves, sticks, soaps or any other appropriate vehicles. Thus, the chosen lithium compound may be incorporated, optionally together with other active substances, with one or more conventional carriers, excipients or formulation aids. Suitable compositions include, for example, those disclosed in EP-A-0289204 (Efamol Holdings PLC).

In a fourth aspect, the present invention therefore provides a topical pharmaceutical composition for use in the treatment and/or prophylaxis of Molluscum Contagiosum, said composition comprising a physiologically acceptable lithium compound together with at least one pharmaceutically acceptable carrier or excipient.

Benefits in lithium delivery may also be obtained by formulating the lithium with a skin penetration-assisting or keratolytic agent to aid transdermal passage of the lithium. Suitable keratolytic agents may be basic or acidic and include urea and salicylic acid. Suitable skin penetration-assisting agents include dimethylsulphacetamide or more preferably dimethylsulphoxide (DMSO).

Such pharmaceutical compositions comprising a physiologically acceptable lithium compound together with at least one keratolytic and/or skin-penetration-assisting agent and at least one pharmaceutically acceptable carrier or excipient form a fifth aspect of the invention.

The precise concentrations of lithium in the topical compositions of the invention will depend of course on a number of factors including for example, the severity of the condition to be treated, the form of lithium used and the physical nature of the pharmaceutical composition. Generally, however an effective lithium concentration in the composition is 0.001 to 10% lithium ion, preferably 0.005 to 5%, and most especially preferably 0.3 to 2%.

The invention will now be described with reference to the following non-limiting examples in which all percentage, parts and ratios are by weight unless otherwise specified:

EXAMPLES

The Examples which follow illustrate the practice of this invention. In all cases the patients were treated twice daily with lithium succinate ointment (LSO) containing 8% lithium succinate in a wool alcohols ointment base.

EXAMPLE 1

A four month old boy presented with 13 MC lesions on the trunk and arms: repeated crops of these lesions had appeared over the previous four months. LSO was applied twice daily to the lesions and to the surrounding skin. After six weeks there were only two lesions and after 12 weeks none.

EXAMPLE 2

A four month old boy presented with severe MC with 55 lesions on the axillae, groins and legs. These were obviously causing him severe distress. Only 8 remained after six weeks treatment with LSO and all lesions were eliminated after 12 weeks.

EXAMPLE 3

A 2 year old boy presented with MC. He had 16 lesions on various parts of the body. New lesions had been appearing over the previous two months. He was treated twice daily with LSO ointment. After 11 weeks only 6 lesions were left, after 17 weeks 3 lesions, and after 24 weeks the skin was completely clear.

EXAMPLE 4

A seven year old girl with persistent MC which had lasted for over a year presented with 14 lesions. After 12 weeks only four lesions were left and after 24 weeks all lesions had disappeared.

EXAMPLE 5

A five year old girl who had had persistent MC for over a year presented with 9 lesions on the buttocks. All lesions disappeared after treatment with LSO for 10 weeks.

The examples which follow illustrate pharmaceutical compositions according to the invention:

EXAMPLE 6

A gel formulation comprising carbopol 934A (Goodrich), a gelling agent is prepared having the following composition:

| Lithium succinate | 7% by weight |
| --- | --- |
| Urea | 10% by weight |
| Carbopol 934P | 1% by weight |
| Dimethylsulphoxide (DMSO) | 65% by weight |
| Triethanolamine - qs to pH | 6.8% (approx. 0.15 ml) |
| Distilled water ad | 100% by weight |

A solution of lithium succinate in DMSO is prepared and is admixed with the remaining components in conventional manner.

EXAMPLE 7

A gel composition comprising salicylic acid as the keratolytic agent is prepared with the following composition:

| Lithium succinate | 7% by weight |
| --- | --- |
| Salicylic acid | 2% by weight |
| Klucel HF | 2.5% by weight |
| Dimethylsulphoxide | 65% by weight |
| Macrogol 300 | 18% by weight |
| Distilled water ad | 100% by weight |

I claim:

1. A method of treatment and/or prophylaxis of the human or animal body to combat Molluscum Contagiosum, said treatment comprising topically administering a therapeutically or prophylactically effective amount of a physiologically acceptable lithium compound to an area on said body affected by Molluscum Contagiosum.

2. A method as claimed in claim 1 wherein said lithium compound is a water and/or lipid soluble lithium salt.

3. A method as claimed in claim 2 wherein the lithium salt is selected from the group consisting of lithium succinate, lithium chloride, lithium carbonate, lithium orotate and lithium salts of polyunsaturated fatty acids.

4. A method as claimed in claim 3 wherein said lithium salt is lithium gammalinolenate or lithium dihomogammalinolenate.

5. A method as claimed in claim 1 wherein said lithium compound is administered as a composition comprising 0.001 to 10% lithium ion.

6. A method as claimed in claim 5 wherein said administered composition comprises 0.3 to 2% lithium ion.

7. A method of treatment and/or prophylaxis of the human or animal body to combat Molluscum Contagiosum, said treatment comprising topically administering to an area on said body affected by Molluscum Contagiosum a therapeutically or prophylactically effective amount of a pharmaceutical composition comprising a physiologically acceptable lithium compound together with at least one keratolytic or skin penetration assisting agent and at least one pharmaceutically acceptable carrier or excipient.

8. A method as claimed in claim 7 wherein said keratolytic agent is selected from the group consisting of ureu and salicylic acid.

9. A method as claimed in claim 7 wherein said skin penetration-assisting agent is selected from the group consisting of dimethylsulphacetamide and dimethylsulphoxide.

* * * * *